United States Patent [19]

Meyers et al.

[11] 4,327,742
[45] May 4, 1982

[54] APPARATUS FOR DETECTING TEMPERATURE VARIATIONS OVER SELECTED REGIONS OF LIVING TISSUE, AND METHOD THEREOF

[75] Inventors: Phillip H. Meyers, New Orleans, La.; Franklin R. Greene, Flushing, N.Y.

[73] Assignee: E-Z-EM Company, Inc., Westbury, N.Y.

[21] Appl. No.: 88,159

[22] Filed: Oct. 25, 1979

[51] Int. Cl.³ .............................................. A61B 5/00
[52] U.S. Cl. .................................................. 128/736
[58] Field of Search ............... 128/736; 73/343 B, 356

[56] References Cited

U.S. PATENT DOCUMENTS

| | | | |
|---|---|---|---|
| 3,339,542 | 9/1967 | Howell | 128/736 |
| 4,043,324 | 8/1977 | Shaw | 128/736 |
| 4,060,654 | 11/1977 | Quenneville | 128/736 |
| 4,083,364 | 4/1978 | Kelly et al. | 128/736 |
| 4,186,731 | 2/1980 | Clark | 128/736 |

*Primary Examiner*—William E. Kamm
*Attorney, Agent, or Firm*—McAulay, Fields, Fisher, Goldstein & Nissen

[57] ABSTRACT

An apparatus for detecting temperature variations over selected regions of living tissue is in the form of a low pressure supported pillow structure including a first wall portion of temperature responsive material and a second wall portion of transparent material to permit viewing of the temperature responsive material. The wall portions comprise a fluid chamber including an inflation valve to permit inflating the pillow structure when gaseous fluids are used.

The method of using the pillow structure comprises pressing the temperature responsive film into conformity with the tissue, or portion of other object to be scanned, and viewing the temperature response through the clear wall portion.

The flexible film is preferably also elastic and carries liquid crystals on its inner surface to give it a temperature responsive characteristic. The elastic characteristics of such a sheet of material enhances its ability to closely conform to contoured objects or tissues while minimizing local unequal pressure regions—and thereby minimizing meaningless artifacts in the scan. Disposing liquid crystals on the inner surface permits viewing the temperature variation response while the device is in contact with the patient. The temperature response is visible through the transparent material wall.

Where non-compressible fluids or semi-solids or gels are used to "inflate" the device, elastic characteristics for a wall portion is preferable. As such inflation media do not compress, an elastic wall portion will stretch to allow the temperature sensitive film to conform to a protrudence extending thereinto.

9 Claims, 8 Drawing Figures

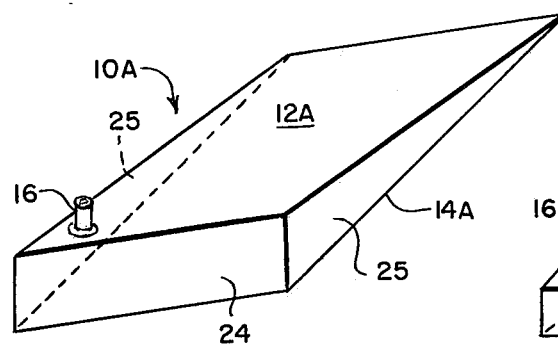
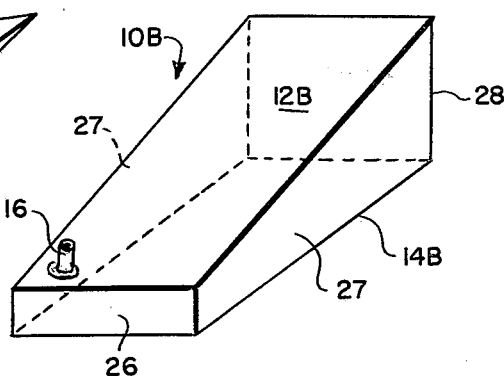
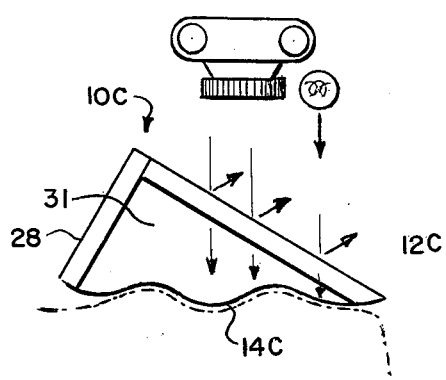
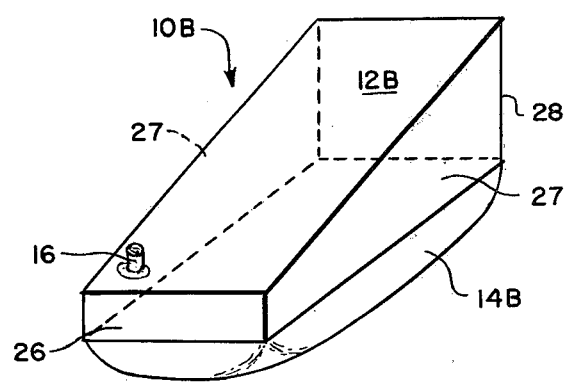
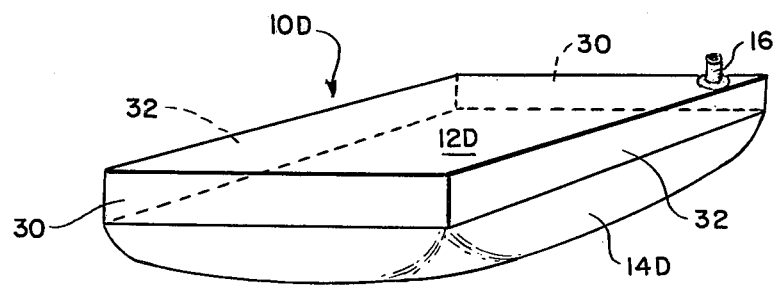

APPARATUS FOR DETECTING TEMPERATURE VARIATIONS OVER SELECTED REGIONS OF LIVING TISSUE, AND METHOD THEREOF

BACKGROUND OF THE INVENTION

In recent years significant progress has been made in the use of thermography as a non-invasive screening technique for the early detection of cancer and as a diagnostic tool for visualizing and locating areas of the human body wherein there is some malady.

Thermographic techniques can be divided into three general types: contact thermography where temperature variations are measured by direct contact with the skin surface, long wave infra-red thermography or electronic thermography, wherein infra-red radiation radiated from the skin surface is detected, for example, using a solid state crystal receiver for wavelengths in the range of (approximately) 8 to 15 microns, and wherein the surface is scanned and an image normally reproduced electronically; and absorption thermography wherein the skin is irradiated with short wave infrared radiation and a photographic of the energy reflected from the body taken on infra-red film.

Thermographic techniques dealing with infra-red radiation which is reflected from the body being scanned, are not generally used clinically although variations thereof (including techniques using micro-waves rather than infra-red radiation) are presently being studied. Infra-red (or other similar radiation) is directed against the skin surface, and may penetrate the skin a short distance. Energy not absorbed is radiated and the resulting image has some diagnostic uses.

The present invention is concerned with contact thermography wherein heat generated by the body's processes is measured directly. Long wave infra-red or electronic thermography measures heat generated by the same phenomenon except that measurement is made by measuring infra-red radiation above the skin rather than by direct contact with the skin.

Long wave infra-red or electronic thermography has been found very useful as a diagnostic tool and much recent work has been done in studying lower back injuries. The results of applying thermographic techniques to detect lower back injuries, and especially to Lumbar Disc Disease, have been found to be comprable to more standard techniques. However, as an initial diagnostic tool, these thermographic methods have the overwhelming advantage of being noninvasive and easily accomplished. See, for example, "Thermography of the Spine," *Applied Radiology*, September-October 1976 (pages 103-105); and "Peripheral Thermographic Manifestations of Lumbar-Disc Disease," *Applied Radiology*, September-October 1978; where thermographic techniques employing long wave infra-red thermography are described.

Although long wave infra-red or electronic thermography shows great potential for diagnostic purposes, the equipment necessary to make electronic thermographs is relatively expensive, with an average price of about fifty thousand dollars. The device includes an appropriate receiver or sensor for infra-red radiation in the 8-15 micron region, and usually uses moving mirrors to collect radiation over the area of the body to be scanned. The response of the detector is then reproduced as an electronic image analogously to the manner in which an image is prepared on a television set. This may be photographed to provide a permanent record.

In general, thermography is potentially a very powerful diagnostic tool. Temperature rises in various parts of the body can result from any malady against which the body's immune system mounts an attack, including nerve irritation, infection, bone misalignment, so-called auto-immune ailments or other perceived irritations within the body. For example, cancerous cells (Neoplasms) generate heat due to rapid or excessive metabolic processes characteristic thereof. Blood flow variations, due to a blocked or partially blocked artery, or to nerve irritations such as can be caused by Spinal column disc misalignment or cracking—or any other cause, will result in asymetric temperature variation useful as an indication of possible problems. By correlating asymetric temperature variations with previous medical history, and other medical/physiological knowledge, a skilled practitioner is able to diagnose—or at least be aware of probable ailments. This is not unlike the well-known use of general body temperature as an indication of an infection—although thermography is more specific. Although the magnitude of the temperature variation, often only 0.1-0.3 degrees Farenheit, depends on may factors, such temperature variations can often be detected by measurement of temperature variations in the skin.

An important development which has made contact thermography a practical reality was the development of liquid crystals and of methods for supporting liquid crystals on various substrates to form temperature responsive sheets of material. Such materials are described, for example, in U.S. Pat. Nos. 3,619,254 and 3,969,264. These patents disclose methods for preparing suitable liquid crystals carrying films having various substrates. These materials can be used to accomplish similar diagnosis as that formally attainable using expensive thermographic equipment, as outlined above.

The main problem encountered with contact thermographic methods was to ensure good and even contact between the liquid crystals and the skin. Early techniques involved painting a black undercoat directly onto the patient's skin and applying liquid crystals directly to the undercoating. This ensured good and even contact with the skin but was a rather burdensome method involving some discomfort and inconvenience to the patient.

Liquid crystal carrying plates were an improvement over the direct coating method with respect to patient comfort, but were difficult to use with respect to obtaining good and even contact with the skin. This was especially true where highly contoured portions of the skin were being scanned, such as the female breast or highly curved portions of the body frame.

U.S. Pat. Nos. 3,830,224 and 3,847,139 were drawn to devices which endeavored to obtain close contact with the female breast by supporting liquid crystals on a suitable garment such as a brassiere-like device. These were an improvement over the relatively inflexible plates earlier used, but still had limited coverage and were confined to the specific tissue for which they were designed. In addition, the brassiere shape was found to deform the breasts at various points so that, depending on the size and the shape of the woman's breast, some portions of the brassiere did not come into contact with the breast at all while other portions contacted the breasts to such an extent as to deform the breasts thereby producing artifacts or distorted thermograms.

The invention disclosed in U.S. Pat. No. 4,135,497, provides a device which is a simple and effective solution to the problem of close conformity to the tissues, while avoiding the disadvantages of the earlier liquid crystal devices. Basically, the device of U.S. Pat. No. 4,135,497, includes a liquid crystal carrying elastic flexible film which is applied over the complete skin area where the tissues are to be thermographed. Air enclosed between the skin and the film is evacuated through a special valve and spacer arrangement, thereby to cause the liquid crystal carrying film to conform closely to the shape and contour of the skin. The color pattern which forms on the film can then be directly observed and photographed.

Although the device of U.S. Pat. No. 4,135,497 provides close and complete contact with the skin surface which is to be scanned, the method of using the device requires first that the area to be scanned be wrapped with the temperature responsive film; then spacers must be inserted; and evacuation equipment applied to conform the film to the body. In addition, the film must be generally designed for use over the portion of the body intended to be scanned and only has limited use over other tissue portions. Thus the same device may not be useable over other portions of the body.

The present invention incorporates the advantages of the device of U.S. Pat. No. 4,135,497, without the need for special techniques to ensure smooth conformity to the body, and is generally applicable to all portions of the body. The present invention device may even more portable and inexpensive than is the device of U.S. Pat. No. 4,135,497.

BRIEF DESCRIPTION

Briefly, one embodiment of the present invention is a sheet of transparent material to which a sheet of flexible film carrying liquid crystals visible from its inner surface, is secured along its edges to form an air pocket therebetween. A valve is provided through the air pocket when required, so that air can be introduced into the air pocket under low pressure to inflate the device.

In use, the device is inflated causing the sheet of flexible film carrying the liquid crystals to pillow out. The film is pressed against the portion of the patient's body over which it is desired to scan the temperature differences. The device, inflated to a low pressure, acts like a partially inflated child's balloon and will conform closely to the skin against which it is pressed. The liquid crystal temperature variation pattern, visible on the inner surface of the flexible film, can be viewed through the sheet of clear material and can be photographed.

Although it is possible to inflate the device by mouth, that is by blowing through the inflation valve, in practice it has been found that moisture builds up inside of the air pocket making visualization difficult and, occasionally, causing the sheets of material forming the air pocket to stick together. A small, low pressure air pump, such as are used for home aquaria, or bellows, is therefor preferably used for inflating the device. Also, sticking together of the sheets of material can be avoided by using side walls to form a box-like structure to keep the walls away from each other.

The flexible sheet is preferably an elastic sheet as well, to provide the "give" to insure close conformity with various highly contoured portions of the body.

It is also advantageous to make the sheet of transparent material, from a rigid synthetic plastic material which can yield or bend slightly without breaking. This not only results in a robust device, but also provides further flexure-ability or "give" to the device when pressed against tissue to be scanned.

The air valve may be any usual low pressure valve including a short piece of flexible tube which can be clamped to prevent escape of low pressure air contained in the air pocket.

"Inflation" of the device can be accomplished by use of any transparent fluid or semi-solid or gel-like transparent material. A semi-solid inflation medium has the advantage of not leaking. This also eliminates the need for an inflation valve, if desired. However a device permanently filled with a gel is obviously less portable than an air deflatable air filled device. Transparency of the material is necessary to permit viewing the liquid crystals.

BRIEF DESCRIPTION OF THE DRAWINGS

FIG. 4 is a perspective view of an embodiment of the device of FIG. 1, in deflated condition;

FIG. 5 is a perspective view of a further embodiment of the device of FIG. 1, in deflated condition;

FIG. 6 is a perspective view of the embodiment of FIG. 5 in inflated condition;

FIG. 7 is a sectional view similar to FIG. 3, of an embodiment of the device of FIG. 5, with a semi-solid filling media, and without a valve; and FIG. 8 is a perspective view of a still further embodiment of the invention, in partially inflated condition.

DESCRIPTION OF THE PREFERRED EMBODIMENT

Figure 1:
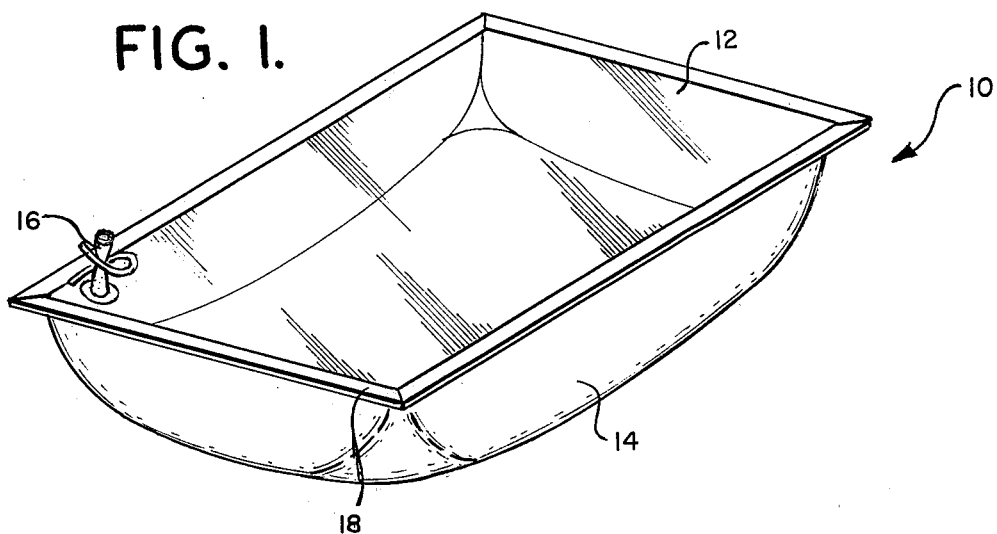
FIG. 1 is a perspective view of the present invention device, in an inflated condition.
Figure 2:
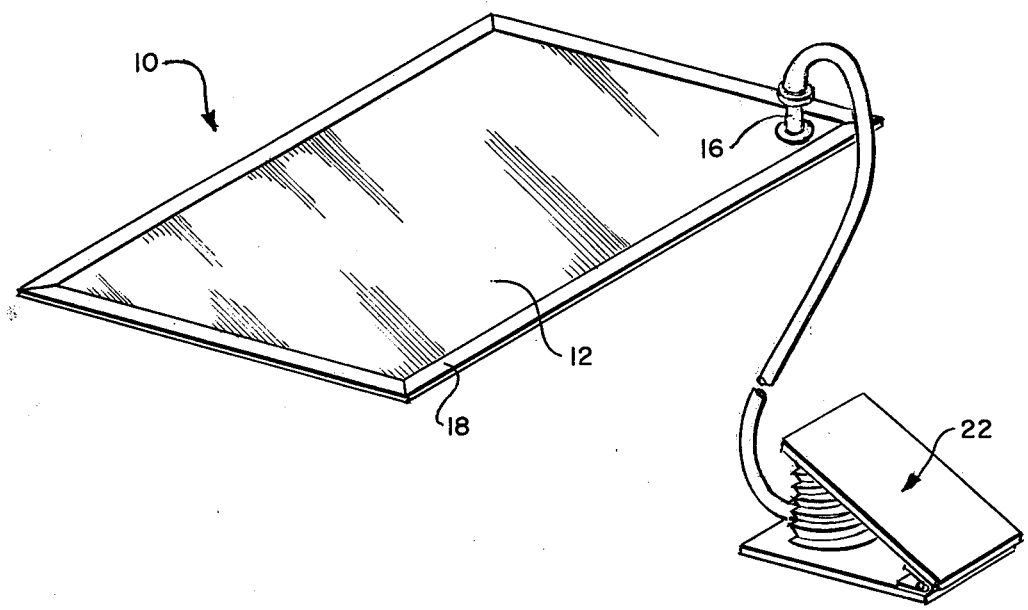
FIG. 2 is a perspective view of the deflated device with an inflation bellows attached for inflation.
Figure 3:
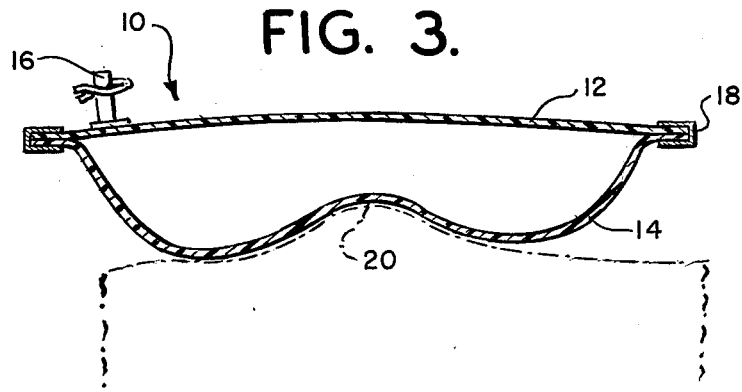
FIG. 3 is a sectional view of the device of FIG. 1, inflated and pressed against tissues shown in phantom.

With reference to FIGS. 1–3, the temperature scan device 10 of this invention is in the form of an inflatable "pillow-like" structure having a sheet of transparent material 12 to which a piece of flexible material 14 is secured along the edges. A valve 16 is provided through the structure, preferably through the clear material sheet 12, to permit introduction of a fluid such as air under low pressure, between the transparent material sheet 12 and the flexible material 14.

The flexible material 14 carries liquid crystals so disposed thereon as to display color changes, in response to different temperatures, on its inside surface visible through the transparent material sheet. Temperature responsive flexible sheets such as are described in U.S. Pat. Nos. 3,619,254 and 3,969,264 have been found particularly suitable although any temperature responsive material which can visualize temperature variation as required, can be employed. Most preferably, these sheets are made with an elastic carrier such as acrylic elastomer.

The transparent material sheet 12 may be of glass or any other transparent material, but is preferably of a slightly flexible synthetic plastic material such as "Lexan" (trademark for thermoplastic carbonate-link polymers, produced by reacting bisphenol A and Phosgene, of General Electric Company, 1 River Road, Schenectedy, New York). Materials such as Lexan may be transparent, have some flexibility, and have the distinct advantage over glass of being relatively non-breakable.

Because this embodiment uses relatively low pressure contained within the air pocket formed between transparent material sheet 12 and the elastic flexible material 14 carrying the liquid crystals, the seal 18 along the edges of these layers can be accomplished by any one of a large number of methods. Thus, for example, adhesive tape can be used or heat sealing or various adhesives, depending on the properties of the sheets being used to form the device.

With reference to FIG. 3, the inflated temperature scan device 10 is pressed against the tissue 20 to be scanned, so that the flexible elastic material film 14 conforms closely to the surface of the tissues 20 to be scanned. Changing color patterns visible on the inner surface of the flexible material film 14 can be observed through the transparent material sheet 12.

When it is intended to photograph the liquid crystal patterns, it may be advantageous to have a non-aligned or skew relationship between the transparent material sheet 12 and the elastic flexible material carrying the liquid crystals 14, as the effect of light reflecting off the clear sheet 12 can thereby be minimized. Embodiments such as are shown in FIGS. 4–7 illustrate structures especially useful where photographs are to be taken. FIG. 4 shows a device 10A which incorporates an end wall 24 and side walls 25 glued or otherwise secured to the clear material sheet 12A to form a triangular device when non-inflated; FIG. 5 shows a device 10B which incorporates two non-equal end walls 26, 28 with side walls 27, to gain the same effect but with a trapazoidal device. As FIG. 6 shows, the inflated trapazoidal shaped device and analogously, the triangular shaped device—supports the flexible sheet 14 in non-alignment with the transparent sheet 12. Thus, in use, as illustrated, in FIG. 7, when the flexible sheet 14 is pressed against the body, the transparent sheet is at an angle. Ideally, the angle should be about 45°, although considerable variation from this is usual. Photographic illumination glare is thereby reflected away permitting photographs to be taken with a minimum of glare.

The device 10C of FIG. 7 differs from the device 10B of FIGS. 5 and 6 in that the device 10C is permanently inflated with semi-solid gel-like material 31 and therefore does not require an inflation valve 16. FIG. 8 shows a symetrical box-like embodiment of the device 10D in partially inflated condition. Side walls 30, 32 serve to keep sheets of material 12D, 14D from contacting each other when the device is deflated. One inch high walls 30, 32 have been found adequate for this purpose. Inflation can be accomplished through valve 16.

The pillowed device is then pressed against the area to be scanned. Employing a semi-rigid transparent material sheet 12, facilitates handling the device 10 during this step, by providing a convenient structure to press against. However, the device can be formed without a semi-rigid front sheet 12, for example, completely of flexible material, like a balloon or beach ball, having one portion of flexible material carrying liquid crystals visible on its inner wall, and another portion transparent for viewing the liquid crystals. The embodiments of FIGS. 4–6 and 8 are used in the same manner. The embodiment 10C is permanently inflated or filled with a transparent semi-solid gel-like material 31.

When a liquid or semi-solid transparent material is used in the "inflatable" device, either a wall portion will need to be elastic, or some provision for release of material through the valve, or an equivalent provision will need to be made to accomodate the non-compressible nature of these materials. Bellows, balloons or other devices can be connected to valve 16, as required, to act as an overflow reservoir.

The patterns formed by variation in temperature can be viewed through the transparent material sheet 14. As noted above, the skew embodiments of FIGS. 4–7 can be used with photographic equipment with the light source directly in front of the screen. However the symmetrical embodiments of FIGS. 1–3 and 8 can also be used if the light source is directed at an angle to reduce reflections.

What is claimed is:

1. A device for detecting temperature variations over selected regions of living tissue comprising:
    an inflatable chamber having first and second opposed walls,
    said first wall comprising an elastic sheet which carries temperature-responsive liquid crystals,
    said second wall comprising a sheet of transparent material, said second wall being substantially rigid and non-elastic relative to said elastic sheet of said first wall,
    said chamber having an inflated state and a deflated state, said chamber when in said inflated state providing a convex surface defined by said elastic sheet.

2. The device of claim 1 wherein said sheet of transparent material, in said inflated state of said chamber, is substantially flat.

3. The device of claims 1 or 2 comprising: a valve extending through a wall of said chamber to permit inflation and deflation of said chamber.

4. The device of claim 3 wherein said chamber is air inflatable.

5. The device of claims 1 or 2 further comprising: a substantially rigid frame, the periphery of said sheet being attached to and defined by said frame.

6. A device for detecting temperature variations over selected regions of living tissue comprising:
    an inflatable chamber having first and second opposed walls,
    said first wall comprising a flexible sheet which carries temperature-responsive liquid crystals,
    a substantially rigid frame, said sheet being attached to said frame,
    said second wall comprising a sheet of transpatent material, said second wall being substantially rigid and relative to said flexible sheet of said first wall,
    said chamber having an inflated state and a deflated state, said chamber when in said inflated state providing a convex surface defined by said flexible sheet.

7. The device of claims 1, 2 or 6 further comprising:
    a substantially rigid side wall extending between said first and second opposed walls, waid side wall determining a minimum spacing between said first and second opposed walls.

8. The device of claims 1, 2 or 6 wherein said chamber is inflated with a gel-like material.

9. The method for detecting temperature variation in selected regions of living tissue comprising the steps of:
    inflating a chamber having first and second opposed walls wherein the first wall includes an elastic sheet which carries temperature-responsive liquid crystals and in which the second wall includes a sheet of transparent material, the second wall being substantially rigid and non-elastic relative to the elastic sheet of the first wall, said step of inflating causing said elastic sheet to pillow outwardly and provide a convex surface, pressing the convex surface of said flexible sheet against the tissue to be examined and conforming said film to the tissue surface, and observing, through said transparent material of said second wall portion, the color pattern display of the liquid crystals in said first wall portion.

* * * * *